US007878425B2

(12) United States Patent
Handzel et al.

(10) Patent No.: US 7,878,425 B2
(45) Date of Patent: Feb. 1, 2011

(54) LIQUID SUPPLY ATTACHMENT FOR SPRAY GUN

(75) Inventors: James J. Handzel, Golden Valley, MN (US); Joseph W. Kieffer, Chanhassen, MN (US); Christopher J. Sulzer, Minneapolis, MN (US); Christopher W. Carleton, Eden Prairie, MN (US)

(73) Assignee: Wagner Spray Tech Corporation, Plymouth, MN (US)

( * ) Notice: Subject to any disclaimer, the term of this patent is extended or adjusted under 35 U.S.C. 154(b) by 219 days.

(21) Appl. No.: 12/256,647

(22) Filed: Oct. 23, 2008

(65) Prior Publication Data

US 2009/0108089 A1 Apr. 30, 2009

Related U.S. Application Data

(60) Provisional application No. 61/000,390, filed on Oct. 25, 2007.

(51) Int. Cl.
*B05B 7/30* (2006.01)
*A61M 11/02* (2006.01)
*B05B 7/04* (2006.01)

(52) U.S. Cl. .......................... 239/346; 239/8; 239/320; 239/322; 239/373; 239/525; 220/495.02; 220/495.06; 141/2; 141/4; 141/5; 141/7

(58) Field of Classification Search ................. 239/346, 239/379, 373, 375, 378, 526, 527, 528, 320–322
See application file for complete search history.

(56) References Cited

U.S. PATENT DOCUMENTS 888,693 A * 5/1908 Aranguren et al. .......... 239/305
3,157,360 A * 11/1964 Heard ........................ 239/354
3,270,920 A * 9/1966 Nessler ........................ 222/95
4,756,481 A * 7/1988 Leuenberger ............... 239/332
4,989,787 A * 2/1991 Nikkel et al. ................ 239/346
5,236,128 A * 8/1993 Morita et al. ............... 239/407
5,415,352 A * 5/1995 May ........................... 239/365
5,667,142 A * 9/1997 Newman .................... 239/346
6,540,835 B2 * 4/2003 Kim et al. ................... 118/668
7,350,723 B2 * 4/2008 Reedy ........................ 239/332
7,513,443 B2 * 4/2009 Escoto et al. ............... 239/328
7,798,427 B2 * 9/2010 Joseph et al. ............... 239/346
2007/0102458 A1 * 5/2007 Valley ........................ 222/334

* cited by examiner

*Primary Examiner*—Len Tran
*Assistant Examiner*—James S Hogan
(74) *Attorney, Agent, or Firm*—Nikolai & Mersereau, P.A.; Thomas J. Nikolai

(57) ABSTRACT

A conventional liquid spray gun having a compressed air supply equipped with a liquid, e.g. paint, container for supplying the liquid to be sprayed onto a target surface. The container has a closed bottom, an open top and a cylindrical sidewall. A removable cover is attached over the open top of the container, and the cover has a pair of apertures extending through it, one of which holds a proximal end of a rigid tube whose distal end extends to a point close to the container's bottom. Slidingly mounted on the rigid tube is a generally circular, movable plunger whose periphery engages the cylindrical sidewall of the container. Pressurized air injected through the second aperture in the cover forces the plunger against the liquid's surface and causes the liquid to flow through the lumen of the rigid tube to the liquid inlet port of the spray gun.

23 Claims, 5 Drawing Sheets

LIQUID SUPPLY ATTACHMENT FOR SPRAY GUN

CROSS-REFERENCE TO RELATED APPLICATIONS

This application is a non-provisional application claiming the benefit of U.S. Provisional Application Ser. No. 61/000,390, filed Oct. 25, 2007, and which is deemed incorporated by reference herein in its entirety.

BACKGROUND OF THE INVENTION

I. Field of the Invention

This invention relates generally to liquid supply apparatus for spray guns, and more particularly to an air pressure-assisted liquid supply apparatus attachable to a liquid input port of a spray gun.

II. Discussion of the Prior Art

Various liquid supply devices are known in the art for supplying mixtures of component liquids to be sprayed via air-powered spray guns, such as those commercially available from Sata Farbspritzechnik GmbH & Co., Lex-Aire Products, Inc. of North Billerica, Mass., Graco, Inc. of Minneapolis, Minn., and a model available from Wagner Spray Tech Corporation of Minneapolis, Minn.

U.S. Pat. Nos. 6,752,179, 6,796,514 and 6,953,155 each describe a cup-like assembly for feeding liquid to the inlet port of such spray guns. In each of those patented arrangements, the liquid to be sprayed is contained within a collapsible polymeric bag and the bag is, in turn, disposed in a rigid cup-like housing. An adapter designed to mate with the inlet connection of a particular spray gun is in fluid communication with the contents of the bag. When air under pressure is introduced in the space between the bag and the rigid housing, the bag is compressed forcing the liquid contents thereof out through the adapter and into the inlet port of the spray gun with which the liquid feeding assembly is attached.

In so-called "gravity-fed units", the liquid inlet for the spray gun projects upward from the barrel of the gun and the cup assembly with its tubular adapter is inverted when joined to the gun's inlet. Gravity and/or the Venturi-effect produced by high velocity flow air through a nozzle are used to draw the liquid from the flexible bag and into the air stream ultimately exiting the barrel of the spray gun. Again, as the liquid is extracted from the flexible bag, it collapses. Here, reference is made to the Schwartz U.S. Pat. No. 6,796,514 as an example of a prior art gravity-fed spray gun.

One problem associated with gravity feed is that the spray pattern tends to be position sensitive. That is to say, when the liquid supply cup is disposed above the gun barrel, an adequate stream of liquid is drawn from the cup and mixed with the air stream to provide a full coverage pattern. However, if the shape of the object being treated, e.g. spray painted, necessitates inverting the gun such that the supply cup is disposed below the gun barrel, the suction force due to the Venturi nozzle may be insufficient to draw an adequate quantity of the liquid, creating an uneven pattern.

Accordingly, a need exists for an improved pressurized liquid supply device for use with a spray gun.

SUMMARY OF THE INVENTION

In accordance with a first embodiment of the invention there is provided a rigid plastic or metal container having a cylindrical sidewall, a closed bottom and an open top with a removable cover closing the container's open top. The cover has first and second apertures formed through its thickness dimension. A generally rigid tube extends through the first aperture and extends toward, but short of, the container's closed bottom. A movable plunger is slidably disposed on the rigid tube and is dimensioned to wipe against the cylindrical sidewall of the container as the plunger is made to move from a first position proximate the removable top to a second position proximate the closed bottom such that the plunger's descent displaces liquid from the container through a lumen of the rigid tube. Means are provided for attaching the container to an air-operated spray gun such that liquid passing through the lumen of the rigid tube feeds the liquid to the spray gun. A connection is made between the spray gun and the second aperture in the cover allowing pressurized air to enter the container at a location above the movable plunger to thereby force the plunger downward against the surface of the liquid in the container.

In a further embodiment, a disposable, single-use liner is provided that closely conforms to the bottom and cylindrical sidewall of the rigid container, the use of which facilitates clean-up of the container assembly following job completion or a desired paint color change.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1A:
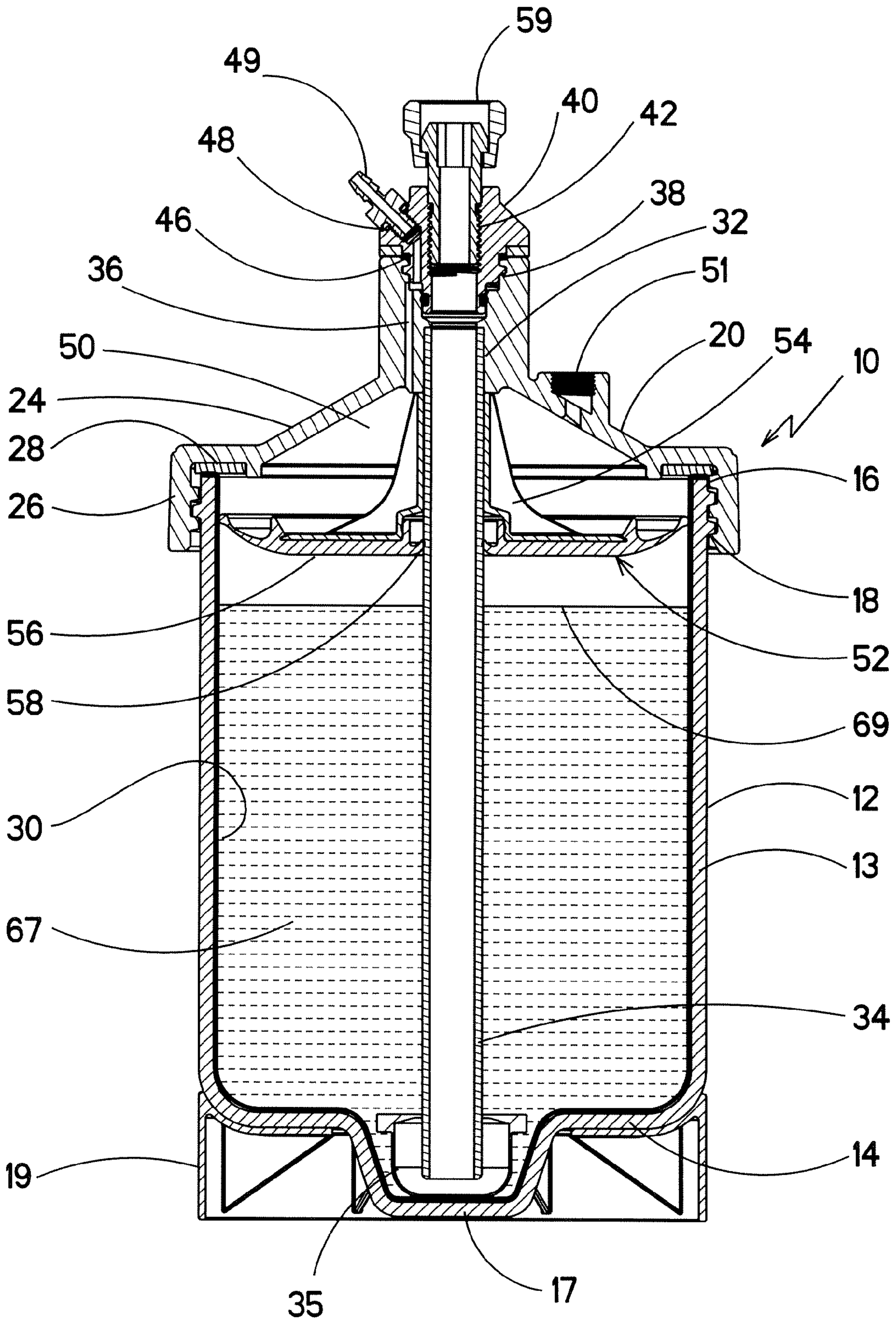
FIG. 1*a* is a longitudinal cross-sectional view taken through the center of the cup assembly with the plunger proximate the top of the cup.

Certain terminology will be used in the following description for convenience in reference only and will not be limiting. The words "upwardly", "downwardly", "rightwardly" and "leftwardly" will refer to directions in the drawings to which reference is made. The words "inwardly" and "outwardly" will refer to directions toward and away from, respectively, the geometric center of the device and associated parts thereof. Said terminology will include the words above specifically mentioned, derivatives thereof and words of similar import.

Figure 4:
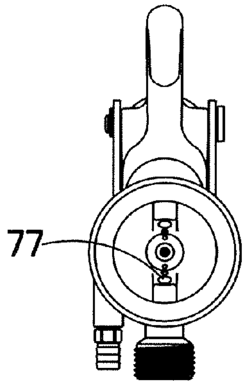
FIG. 4 is a front end view of the spray gun.
Figure 3:
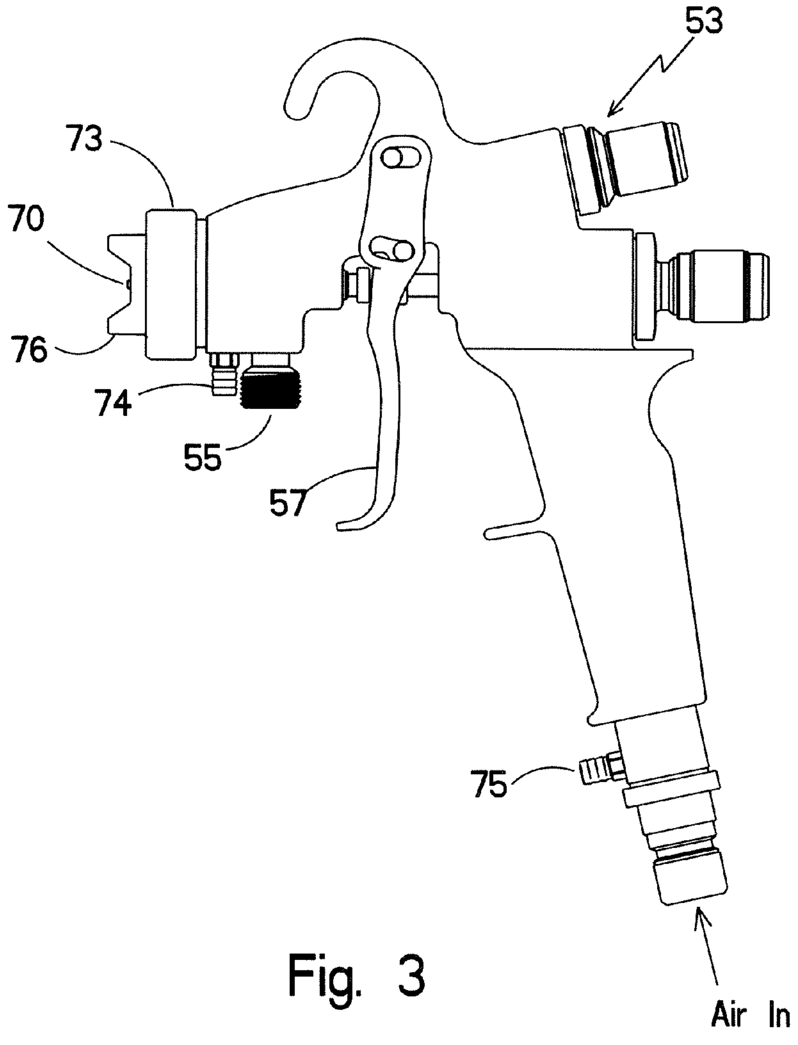
FIG. 3 is a side elevation view of a spray gun with which the present invention finds use.

Referring first to FIG. 1*a*, there is illustrated a liquid supply apparatus adapted for attachment to a commercially-available air-operated spray gun, such as shown in FIGS. 3 and 4. The liquid in question may be a paint mixture, an adhesive or any one of a number of liquids to be applied as a coating on a substrate. For convenience, throughout the following description, the liquid will be referred to as spray paint that typically includes a pigment mixed with a volatile solvent that is of a viscosity permitting it to be applied as a fine spray when entrained in an air stream controlled by a pistol-like spray gun.

Figure 2:
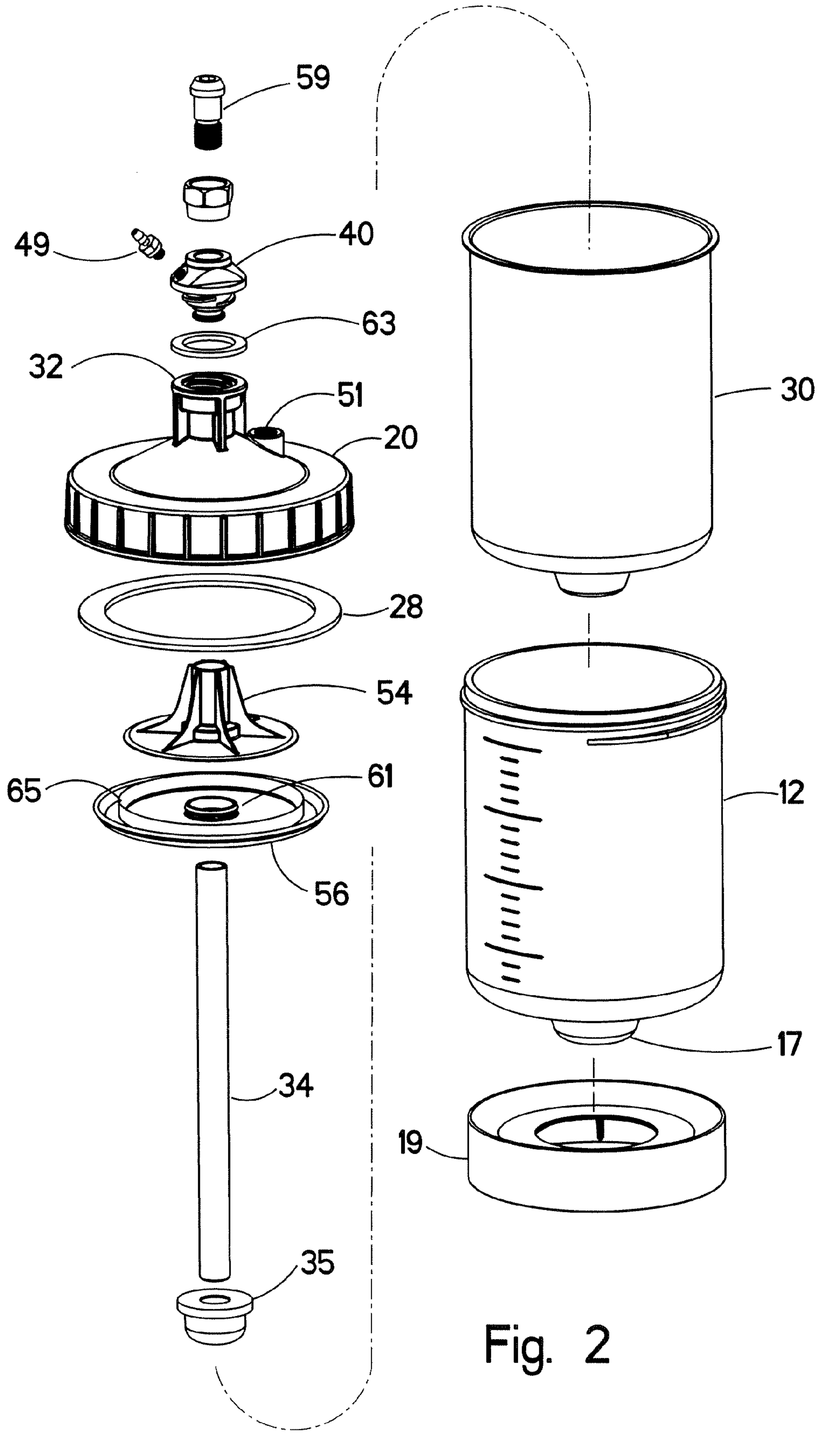
FIG. 2 is an exploded view of the embodiment of FIG. 1*a;*

The liquid supply attachment is indicated generally by numeral 10 and is seen to comprise a cylindrical cup 12 having a closed bottom end 14 and an open upper end 16. The lower end is shown as including a recessed portion 17 in FIG. 1*a*. A base member 19 fits onto the bottom of the cup permitting the cup to better stand upright on a flat surface. The cup member 12 may be fabricated from a suitable rigid plastic or a metal, such as aluminum, and it is provided with external threads 18 located proximate its periphery at the upper end 16. The cup is preferably formed from a transparent plastic allowing the user to view the contents of the cup as a spray paint job progresses. Graduated markings as shown in FIG. 2 may also be provided to indicate the volume of paint present at any given time.

After the cup has been filled with paint to be sprayed, the open upper end of the cup member 12 is adapted to be closed by a cover member 20, which is designed to rest upon the upper edge surface of the cup 12 having an upper surface 24 and a downwardly depending cylindrical flange 26 that is internally threaded so as to mate with the threads 18 of the cup member 12. An O-ring or a flat gasket type seal 28 is placed between the cover member 20 and the upper edge of the cup member 12 so that when the cover member 20 is screwed down, a seal is created preventing escape of the liquid contents of the cup member 12.

With continued reference to FIG. 1*a*, disposed within the cup member 12 and closely adhering to the cylindrical sidewall 13 and the bottom wall 14 is an optional molded plastic liner 30 represented by a heavy black line in the drawing. The liner may be disposable after a single use which obviates the need for cleaning the interior wall surface of the cup 12 between successive uses. Because the liner 30 need not be collapsed, as in the cited 3M patents, it can be made to have a thicker wall if reuse is desired. As can be further seen in FIG. 1*a*, the upper rim of the liner 30 is captured between the cover 20 and the upper edge of the cup member 12 and provides a seal that precludes spray paint or the like from finding its way between the inner wall of the cup member 12 and the outer wall of the liner 30.

The cover member 20 has a frusto-conical dome shape that includes a central bore 32 into which is fitted a generally rigid or semi-rigid tube 34. The tube 34 extends toward, but ends just short of, the bottom wall 14 of the cup member 12 so that its lumen is not occluded by the bottom end 14. An optional basket-shaped screen filter 35, that fits within the recess 17 formed in the bottom end 14, is frictionally attached to the lower end of rigid tube 34. The filter precludes thickened globs of paint from entering the tube 34 and possibly occluding the spray gun's needle valve. The cover member 20 further includes a second bore 36 extending parallel to the bore 32 in which the tube 34 is made to fit. The bore 36 serves as an air passage through the thickness dimension of the cover 20, as will be further explained herein below.

Placed atop the cover member 20 and held in place by threads 38, in one embodiment, is an adapter member 40 comprising a double lumen tube. The first lumen 42 extends the length of the adapter 40 and is in fluid communication with the lumen of the tube 34 that extends through the center of the dome 20. The second lumen of the adapter 40 is identified by numeral 46 and extends from an internally threaded opening 48 at the upper end of the adapter 40 to the bottom of the adapter where it is exposed to a chamber 50. A hose nipple 49 fits into threaded opening 48 whereby a short length of hose (not shown) is used to connect to the nipple 49 and to an air outlet 74 of a spray gun, as at 53 in FIG. 3. On some commercially available spray guns, the air outlet fitting is located on the gun's handle, as at 75 in FIG. 3. Alternatively, an air compressor may be coupled to a port 51 leading to the chamber 50. Adapter 40 could also be designed to directly couple to a customized spray gun and include internal passages for both paint and compressed air. This would eliminate the need for external hose to deliver compressed air from the spray gun to the cup assembly.

A plunger, indicated generally by numeral 52, is slidingly mounted with respect to the outer wall of the tube 34 and is seen to include a molded plastic support member 54 to which is attached an elastomeric disk 56. The outer periphery of the elastomeric disk 56 is designed to be somewhat thinner than the portion thereof that is adhered to the support member 54 and is somewhat arcuately shaped to engage the inner wall of the container 12 or the optional liner 30 if one is used. The peripheral edge of disk 56 may be somewhat rounded as on an automobile windshield wiper so as to be able to move well in either an upward or downward direction. Likewise, the portion 58 of the elastomeric disk 56 is also made thinner and curved so as to engage the outer wall of the tube 34 with a wiping action. The choice of materials for the plunger's elastomeric disk 56 may depend on its wear properties as well as the composition of the liquid to be sprayed so that there will be chemical compatibility.

When the nipple 49 of the adapter 40 is coupled by tubing to an air outlet port 74 or 75 of the spray gun 53 and a quick-connect fitting 59 is connected to the liquid inlet connection 55 of the spray gun for which the adapter has been designed, and the trigger 57 of the spray gun is squeezed, air under pressure is made to flow through the lumen 46 in the adapter and the bore 36 in the cover member 20 to develop or maintain a positive pressure on the upper surface of the plunger 52. This will urge the plunger 52 to slide down along the tube 34 and, in doing so, will force the paint in the cup 12 up through the filter 35 and the lumen of the tube 34, through the dome of the cover 20 and up through the lumen 42 of the adapter and from there into the spray gun. A one-way check valve can be used in the tubing between nipple 49 and port 74 or 75 on the gun to maintain pressure in the cup for most consistent spraying as the gun is triggered and released, or as the compressed air supply to the gun is removed and reapplied. Note also that port 51 exists to cover member 20 to allow a pressure relief device to be used to limit pressure in the cup assembly.

Figure 1B:
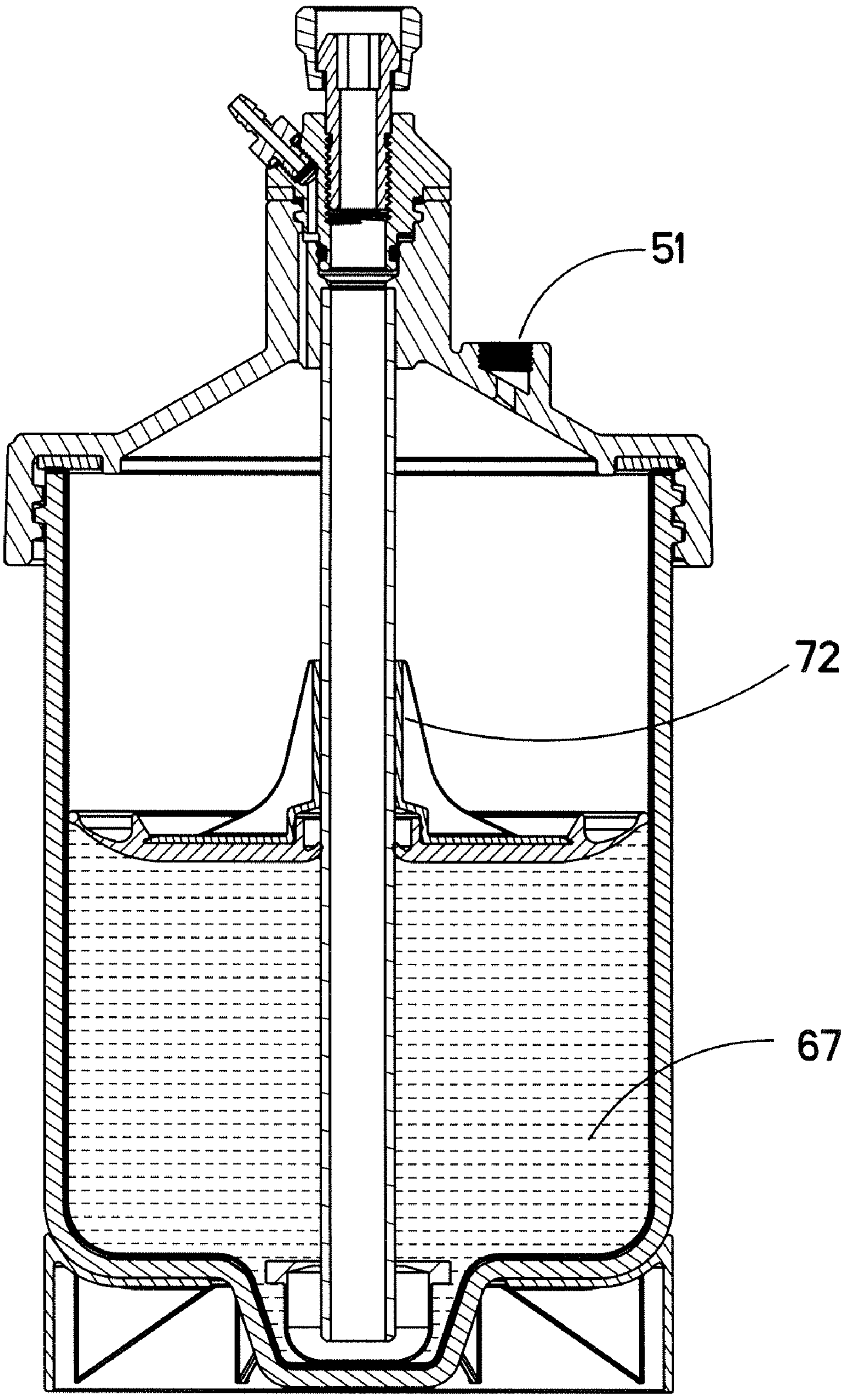
FIG. 1*b* is similar to FIG. 1*a* but with the plunger proximate the midpoint of its travel.
Figure 1C:
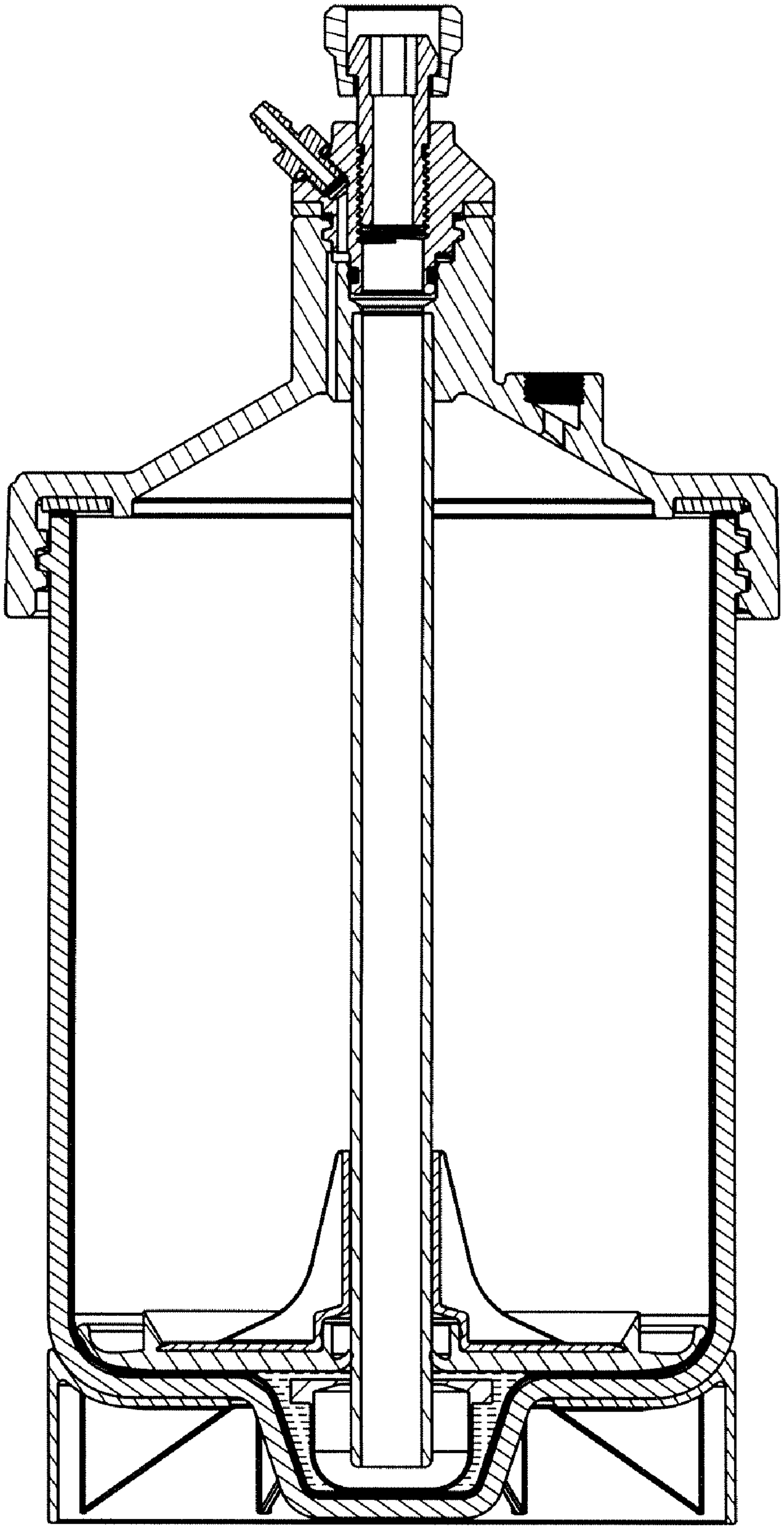
FIG. 1*c* is a view like FIG. 1*a* but with the plunger proximate the bottom of the cup.

Turning next to FIG. 2, the exploded view of the embodiment of FIGS. 1*a*-1*c* enables one to see the individual parts thereof.

FIG. 2 also shows with greater clarity the manner in which the elastomeric disk 56 is joined to the support member 54 and the way in which the elastomeric disk 56 is arranged to wipe against the tube 34 as the plunger member 52 is made to descend. It should be noted that the space above the inner curved portion of the elastomeric disk where it seals to the outer diameter of the tube 34 is exposed to air pressure above the plunger 52 to thereby provide a pressure-activated seal to the tube 34. Other seal arrangements in this area can also be made.

Formed on the upper surface of the disk 56 is a concentric annular protrusion 65 (FIG. 2) designed to engage and grip the peripheral edge of the support member 54. A similar protrusion 61 engages the support member 54 proximate its center opening.

Also seen in FIG. 2 is a seal ring 63 that fits between the adapter 40 and the central stem of the cover 20 to preclude leakage at the joint between the two.

In an alternative embodiment, the liner 30 in FIG. 1*a* is absent. That is, the liner 30 is not essential, but the use thereof is a convenience that eliminates the necessity of cleaning the cup member 12 following each use thereof. The liner can simply be discarded.

FIG. 1*a* shows the liquid cup attachment for the spray gun where the plunger assembly 52 is elevated and the cup 12 is filled with paint or other liquid 67 to be dispensed via a spray gun. In FIG. 1*b*, air pressure exerted on the upper surface of the plunger 52 has forced it down to a midway position in the cup 12, causing the paint to flow up through the lumen of the tube 34 and to thereby enter the spray gun where it mixes with the air stream to form an aerosol spray. FIG. 1*c* shows the plunger fully displaced.

To displace the air present between the upper paint surface 69 and the bottom of the plunger 52 as seen in FIG. 1*a*, once the cup is coupled to a spray gun 53, the operator need only invert the gun and cup so the bottom of the cup is pointed upwards and pull the gun's trigger 57 to move the plunger and force the air from the cup through the same passage as the paint will eventually flow.

Once the plunger has reached the bottom of its stroke as seen in FIG. 1*c*, to cause it to again rise, the operator need only disconnect the air tube (not shown) used to connect the compressed air source to the port 49, unscrew the air cap ring 73 slightly so the nozzle 70 is recessed within the air cap 76 and cover the spray gun's air outlet orifices in the cap 73 as the trigger is pulled. This causes the compressed air from the inlet of the gun to be diverted down the lumen of the tube 34 which pressurizes the underside of the plunger, causing it to move upward toward the top member. As seen in FIG. 1*b*, the support member 54 has a tubular stem portion 72 whose height dimension is selected to provide a positive stop, preventing the elastomeric disk 56 from rising above the level of the cup's rim 16. As illustrated, the stem portion 72 will engage the cover's undersurface to prevent further upward rise of the plunger, maintaining the elastomeric disk 56 below the rim 16. The procedure may also be used with a partially filled container (FIG. 1*b*) to return the plunger to its topmost position so that the cup can be removed and the remaining contents emptied into a paint storage bucket.

If the cup is fabricated from a metal, such as aluminum or stainless steel such that the level of the contents remaining in the cup cannot be directly viewed, an indication of remaining liquid can be obtained by providing a graduated "dip-stick" that is attached to and moves with the support member 54 and that passes through a fluid-type diaphragm seal in the cover 20.

Those skilled in the art will appreciate that, with the arrangement disclosed in FIGS. 1(*a*) through 1(*c*), the spray gun with the container attached can be held in any of a number of orientations with the base of the container pointed upward, downward or to the side during a spraying operation. Moreover, because the plunger forms an effective seal with respect to the container sidewall and the tubular member 34, the inside of the cover is not exposed to paint which facilitates clean-up following use.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, and without limitation, the cup can be replaced with a larger capacity container, such as a five gallon pressure pot, that would be connected with a length of hose to the hand-held spray gun liquid inlets and where a suitably designed air-pressure actuated plunger is provided that is made to slide down a tubular support in the pressure pot while wiping the interior wall of the pressure pot.

What is claimed is:

1. A liquid supply attachment for a spray gun, comprising:

(a) a rigid cup member having a generally cylindrical sidewall, a closed bottom and an open top defining a chamber for containing a liquid to be sprayed;

(b) a generally circular cover member adapted to be secured to the open top, the cover member including an aperture therethrough;

(c) a rigid tube fitted into the aperture in the cover and extending downwardly toward the closed bottom of the cup;

(d) a plunger member slidably disposed on the rigid tube and engaging the cylindrical sidewall at a location beneath the cover member; and (e) an adapter for mating with a spray gun, the adapter being attached to the cover member and having a first bore aligned with a lumen of the rigid tube, and a second bore in fluid communication with an upper surface of the plunger member whereby the application of air, under pressure, to the second bore causes downward displacement of the plunger member within the chamber and attendant upward displacement of liquid to be sprayed contained in the chamber through the lumen of the rigid tube and the first bore of the adapter.

2. The liquid supply attachment of claim 1 wherein the generally cylindrical cup member includes screw threads proximate the open top; and further including an annular ring member having a downwardly depending cylindrical flange that is internally threaded to mate with said screw threads proximate the open top of the cup member for holding the cover member in place.

3. The liquid supply attachment of claim 2 and further including a seal disposed between the cover member and the rigid cup member proximate the open top of the cup member.

4. The liquid supply attachment of claim 1 wherein the plunger member comprises a centrally located support member having an elastomeric disk adhered to the support member, a peripheral portion of the disk being of lesser thickness than a central portion that is adhered to the support member, the peripheral portion being curved to effectively wipe against an interior of the cylindrical sidewall.

5. The liquid supply attachment of claim 4 wherein the elastomeric disk includes a portion of lesser thickness than the central portion and shaped to wipe along the rigid tube during said downward displacement.

6. The liquid supply attachment of claim 1 wherein the adapter member is secured to the cover member by being threaded onto the cover member.

7. The liquid supply attachment of claim 1 and further including a filter element affixed about a lower end of the rigid tube.

8. A liquid supply attachment for a spray gun as in claim 1 and further comprising:

(a) a disposable liner abutting an interior of the cylindrical sidewall and the bottom of the cup member for shielding the interior sidewall and bottom of the cup member from exposure to the liquid to be sprayed.

9. The liquid supply attachment of claim 8 wherein the generally cylindrical cup member includes screw threads proximate the open top; and further including an annular ring member having a downwardly depending cylindrical flange that is internally threaded to mate with said screw threads proximate the open top of the cup member for holding the cover member in place.

10. The liquid supply attachment of claim 9 and further including a seal disposed between the cover member and the rigid cup member proximate the open top of the cup member.

11. The liquid supply attachment of claim 8 wherein the plunger member comprises a centrally located support member having an elastomeric disk adhered to the support member, a peripheral portion of the disk being of lesser thickness than a central portion that is adhered to the support member, the peripheral portion being curved to effectively wipe against an interior of the disposable liner.

12. The liquid supply attachment of claim 8 wherein the adapter member is secured to the cover member by being threaded onto the cover member.

13. The liquid supply attachment of claim 11 wherein the elastomeric disk includes a portion of lesser thickness than the central portion and shaped to wipe along the rigid tube during said downward displacement.

14. The liquid supply attachment of claim 8 and further including a filter element affixed about a lower end of the rigid tube.

15. A liquid supply attachment for an air-operated spray gun comprising:

(a) a container for a liquid to be sprayed, the container having a cylindrical chamber with a closed base and an open top with a removable cover closing the container's open top, the cover having first and second apertures formed through it;

(b) a generally rigid tube extending into the first aperture and extending toward, but short of, the container's base;

(c) a movable plunger slidably mounted on the rigid tube and dimensioned to wipe against a wall defining the cylindrical chamber as the plunger is made to move from a first position proximate the top to a second position proximate the base and wherein the plunger's movement displaces liquid contained in the cup through a lumen of the rigid tube; and (d) means for attaching the container to an air-operated spray gun such that liquid passing through the lumen of the rigid tube feeds the liquid to the spray gun.

16. The liquid cup attachment as in claim 15 wherein pressurized air exits the spray gun through a passageway leading to the second aperture for displacing the movable plunger from the first position to the second position.

17. The liquid cup attachment as in claim 16 wherein the means for attaching the container to the spray gun comprises an adapter having a first through opening in fluid communication with the lumen of the rigid tube, and a second through opening in fluid communication with the second aperture, a coupling adapted to engage an inlet port of the spray gun and means for coupling the passageway to the second aperture.

18. The liquid cup attachment as in claim 17 wherein the adapter is integrally formed with the removable cover.

19. The liquid cup attachment as in claim 15 wherein the plunger comprises an elastomeric disk of a diameter slightly greater than the diameter of the cylindrical chamber and a support member concentrically affixed to an upper major surface of the elastomeric disk, the support member including a tubular stem adapted to receive the rigid tube therethrough.

20. The liquid cup attachment as in claim 19 wherein the height dimension of the tubular stem is designed to engage the cover to stop further upward displacement of the plunger at a location below the top of the container.

21. The liquid cup attachment as in claim 16 wherein the passageway includes a one-way check valve.

22. A method of supplying a liquid to be sprayed to an air-operated spray gun comprising the steps of:

(a) providing a spray gun having a liquid inlet port;

(b) providing a container filled with a liquid to be sprayed, the container having a base, a cylindrical side wall, an open top and a cover removably affixed over the open top where the cover includes a first and a second aperture therethrough with a rigid tube extending into the first aperture and leading to a location proximate the container's base, the rigid tube slidingly supporting a movable plunger thereon where the periphery of the plunger engages the cylindrical sidewall of the container;

(c) coupling the rigid tube to the liquid inlet port and the second aperture to a source of a pressurized gas; and (d) introducing the pressurized gas into the container to effect displacement of the plunger toward the base and force the liquid from the container through the rigid tube to the inlet port of the spray gun.

23. The method of claim 22 and further including a step of returning the plunger to a starting position by rerouting pressurized air through the rigid tube to a space between the closed base and the plunger.

* * * * *